US012201855B2

United States Patent
Fujii et al.

(10) Patent No.: US 12,201,855 B2
(45) Date of Patent: Jan. 21, 2025

(54) PARTICLE BEAM THERAPY SYSTEM AND MAGNETIC RESONANCE IMAGING APPARATUS

(71) Applicant: Hitachi High-Tech Corporation, Tokyo (JP)

(72) Inventors: Yusuke Fujii, Tokyo (JP); Manabu Aoki, Tokyo (JP); Masumi Umezawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 261 days.

(21) Appl. No.: 17/760,548

(22) PCT Filed: Jun. 24, 2020

(86) PCT No.: PCT/JP2020/024901
§ 371 (c)(1),
(2) Date: Mar. 15, 2022

(87) PCT Pub. No.: WO2021/059633
PCT Pub. Date: Apr. 1, 2021

(65) Prior Publication Data
US 2022/0355129 A1    Nov. 10, 2022

(30) Foreign Application Priority Data
Sep. 24, 2019    (JP) ................ 2019-173132

(51) Int. Cl.
*A61N 5/10*    (2006.01)
*A61B 5/055*    (2006.01)

(52) U.S. Cl.
CPC ............ *A61N 5/1071* (2013.01); *A61B 5/055* (2013.01); *A61N 5/1049* (2013.01);
(Continued)

(58) Field of Classification Search
CPC ................ A61N 5/1071; A61N 5/1049; A61N 5/1068; A61N 5/107; A61N 5/1081;
(Continued)

(56) References Cited

U.S. PATENT DOCUMENTS 6,198,957 B1 * 3/2001 Green .................. A61N 5/1042
378/65
8,788,016 B2 * 7/2014 Roell ..................... A61B 5/055
600/411
(Continued)

FOREIGN PATENT DOCUMENTS

JP    2008-543471 A    12/2008
JP    2008-543472 A    12/2008
(Continued)

OTHER PUBLICATIONS

Oborn et al., "Real-time MRI-guided proton therapy", Medical Physics, 44(8), Aug. 2017.
(Continued)

*Primary Examiner* — Peter Luong
(74) *Attorney, Agent, or Firm* — MATTINGLY & MALUR, PC

(57) ABSTRACT

The system includes a bed on which an irradiation target is mounted, an irradiation device that irradiates the irradiation target with a particle beam, and a magnetic resonance imaging apparatus that captures an image of an irradiation object and includes a magnet that generates a static magnetic field in an image capturing space in which the irradiation target is disposed, and a yoke disposed outside the image capturing space and through which a magnetic flux of the generated magnetic field passes. The irradiation device 21 is disposed on a back surface side of the yoke when viewed from the image capturing space, and irradiates the irradiation target with the particle beam from a through-hole or gap provided in the yoke. A direction in which the particle beam
(Continued)

enters the image capturing space intersects with a direction of a static magnetic field applied to the image capturing space by the magnet.

14 Claims, 13 Drawing Sheets

(52) U.S. Cl.
CPC ........... *A61N 5/1068* (2013.01); *A61N 5/107* (2013.01); *A61N 5/1081* (2013.01); *A61N 2005/1055* (2013.01)

(58) Field of Classification Search
CPC ................ A61N 5/1077; A61N 5/1043; A61N 2005/1055; A61B 5/055
See application file for complete search history.

(56) References Cited

U.S. PATENT DOCUMENTS

| | | | |
|---|---|---|---|
| 10,252,083 B2* | 4/2019 | Clayton | ............... A61N 5/1067 |
| 2001/0001807 A1 | 5/2001 | Green | |
| 2008/0144769 A1 | 6/2008 | Schmidt et al. | |
| 2009/0149735 A1 | 6/2009 | Fallone et al. | |
| 2009/0234219 A1 | 9/2009 | Kruip | |
| 2010/0013418 A1 | 1/2010 | Kruip et al. | |
| 2017/0080253 A1 | 3/2017 | Clayton et al. | |
| 2018/0099158 A1 | 4/2018 | Brusasco | |
| 2018/0099160 A1 | 4/2018 | Forton | |
| 2018/0214715 A1* | 8/2018 | Takayama | ............. A61N 5/1042 |
| 2018/0236268 A1* | 8/2018 | Zwart | .................. A61N 5/1067 |
| 2021/0154495 A1* | 5/2021 | Fujii | ........................ A61B 6/02 |

FOREIGN PATENT DOCUMENTS

| | | | |
|---|---|---|---|
| JP | 2009-511222 | A | 3/2009 |
| JP | 4382165 | B2 | 12/2009 |
| JP | 2018-57858 | A | 4/2018 |
| JP | 6519932 | B2 | 5/2019 |

OTHER PUBLICATIONS

International Search Report of PCT/JP2020/024901 dated Aug. 11, 2020.

* cited by examiner

FIG. 2
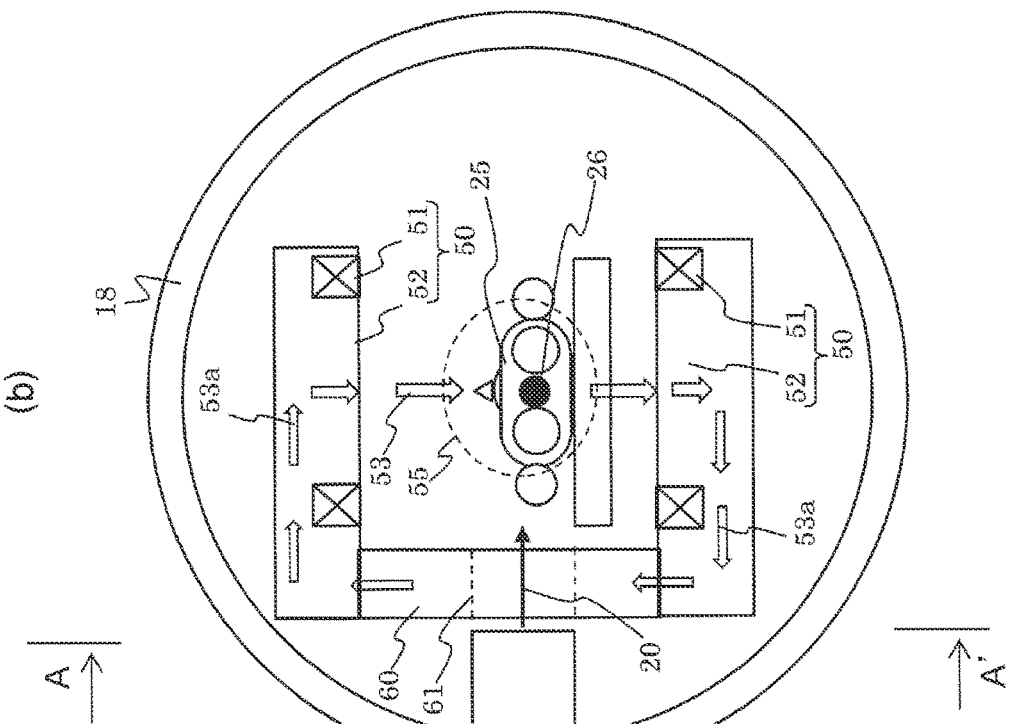
(a) A-A' CROSS-SECTIONAL VIEW
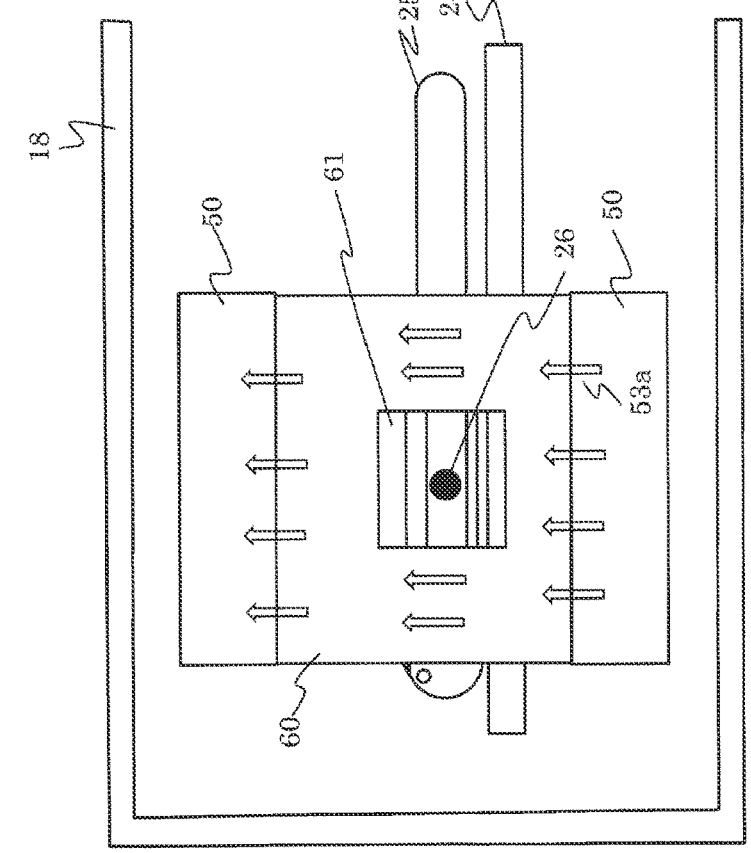
(b)

FIG. 4
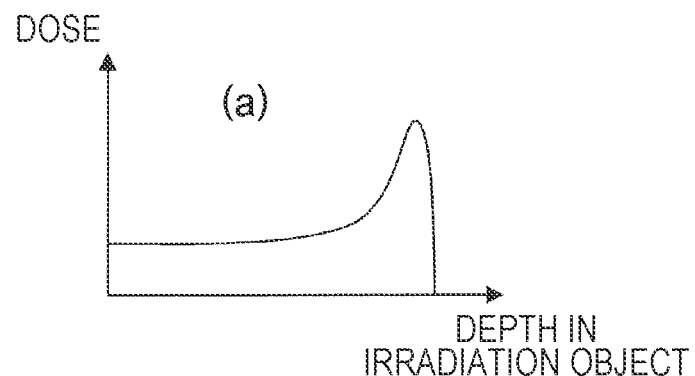
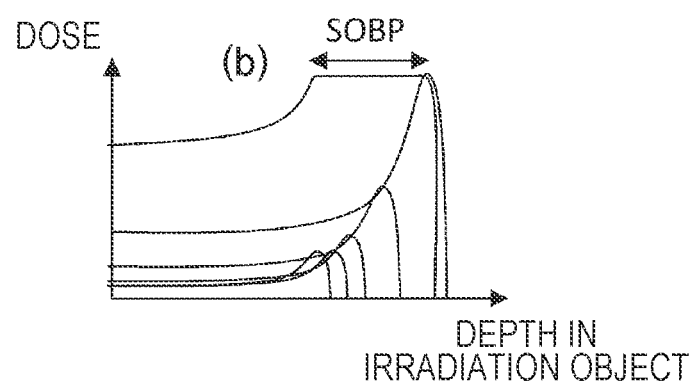
FIG. 5
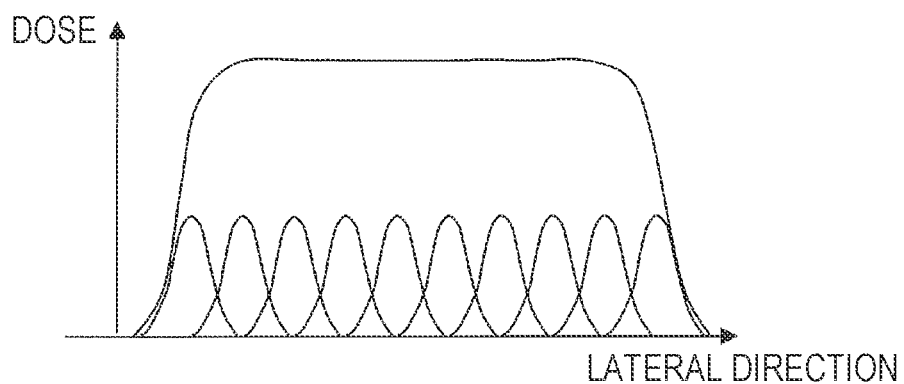

PARTICLE BEAM THERAPY SYSTEM AND MAGNETIC RESONANCE IMAGING APPARATUS

TECHNICAL FIELD

The present invention relates to a treatment apparatus that irradiates an affected area with a charged particle beam (referred to as a particle beam below) such as a proton beam and a carbon beam.

BACKGROUND ART

A particle beam irradiation apparatus that irradiates cancer or the like of a patient with a particle beam is known. The particle beam irradiation apparatus accelerates charged particles by an accelerator to generate a particle beam, transports the particle beam in a beam transport system, and irradiates an affected area of a patient from an irradiation device in a treatment room. At this time, a scanning irradiation method of forming a dose distribution suitable for a shape of an affected area in the body of a patient by scanning a particle beam by a scanning magnet provided in an irradiation device may be used.

When the irradiation target such as the affected area moves by the breathing movement or the like of the patient, it becomes difficult to irradiate the affected area with a particle beam having a dose distribution suitable for the shape of the affected area planned in advance. Thus, in order to form a planned dose distribution, NPL 1 discloses a technique in which a magnetic resonance imaging (referred to as MRI below) apparatus is further mounted on a gantry that rotates around a patient by mounting an irradiation device in a particle beam irradiation apparatus, and an image of a position of a target is captured by the MRI apparatus. If it is detected from the captured MRI image that the target is at a predetermined position (emission allowable range), irradiation with the particle beam is performed at this timing (gate irradiation).

In addition, PTLs 1 and 2 disclose a technique for reducing an influence of a static magnetic field of the MRI apparatus on the trajectory of the particle beam in a manner that the direction of the static magnetic field applied to an image capturing region by the MRI apparatus is made to be substantially parallel to an incident direction of the particle beam in a system in which the MRI apparatus and the particle beam irradiation apparatus are combined.

CITATION LIST

Patent Literature

PTL 1: JP 2008-543471 A
PTL 2: JP 6519932 B

Non-Patent Literature

NPL 1: B. M. Oborn, et al. Med. Phys. 44(8) 2017

SUMMARY OF INVENTION

Technical Problem

The configuration in which the MRI apparatus is mounted on the gantry of the particle beam irradiation apparatus as in the technique disclosed in NPL 1 may cause a problem that a static magnetic field generated by the MRI apparatus leaks to the surroundings of the MRI apparatus and has an influence on the particle beam irradiation apparatus. For example, in order to measure the position and the irradiation quantity of the particle beam with which a target is irradiated, a particle beam monitor is disposed in the irradiation device. In order to reduce the spread of the particle beam after the particle beam passes through the particle beam monitor, the particle beam monitor is desirably disposed at a position as close as possible to the target. However, the particle beam monitor is configured to detect ions and electrons of a gas ionized by the particle beam. Thus, the particle beam monitor is easily influenced by the magnetic field. In addition, when there is a leakage magnetic field of the MRI apparatus, the detection accuracy decreases as the particle beam monitor is disposed closer to the MRI apparatus.

In the technique in PTL 2, in order to irradiate a target with the particle beam through the center of a magnet (coil) of the MRI apparatus, a through-hole is formed in a magnetic shield on the upper surface of the magnet, and the particle beam is caused to pass through the through-hole. In this configuration, the irradiation field size of the particle beam depends on the through-hole size, and it is necessary to increase the through-hole size in order to increase an irradiation field. However, when the through-hole size is increased, the magnetic field of the magnet leaks to the outside of the magnetic shield. Therefore, it is difficult to bring the particle beam monitor close to the magnet. In addition, when the magnetic field of the magnet leaks from the through-hole of the magnetic shield, there is also a problem that it becomes difficult to secure a uniform magnetic field of the image capturing region.

An object of the present invention is to provide a particle beam irradiation system that is equipped with an MRI apparatus and has a configuration in which a particle beam monitor is enabled to be disposed close to the MRI apparatus.

Solution to Problem

In order to solve the above problems, according to the present invention, there are provided a bed on which an irradiation target is mounted, an irradiation device that irradiates the irradiation target with a particle beam, and a magnetic resonance imaging apparatus that captures an image of an irradiation object. The magnetic resonance imaging apparatus includes a static magnetic field generation device. The static magnetic field generation device includes a magnet that generates a static magnetic field in an image capturing space in which the irradiation target is disposed, and a yoke that is disposed outside the image capturing space and through which a magnetic flux of the magnetic field generated by the magnet passes. The irradiation device is disposed on a back surface side of the yoke when viewed from the image capturing space, and irradiates the irradiation target with the particle beam from a through-hole provided in the yoke or a gap provided in the yoke. A direction in which the particle beam enters the image capturing space intersects with a direction of a static magnetic field applied to the image capturing space by the magnet.

Advantageous Effects of Invention

According to the present invention, since the magnetic flux passes through the yoke, it is possible to reduce the strength of a leakage magnetic field outside the yoke. Thus, by disposing the particle beam monitor outside the yoke, it is possible to install the particle beam monitor near the irradiation target. Thus, it is possible to suppress an influence of the magnetic field, and to measure the particle beam by the particle beam monitor with high accuracy.

BRIEF DESCRIPTION OF DRAWINGS

FIG. 2(a) is a cross-sectional view taken along line A-A' parallel to a rotation axis direction, which illustrates arrangement of a rotary gantry 18, a magnet 50, and a yoke 60 in the particle beam irradiation system in the embodiment, and FIG. 2(b) is a front view of the rotary gantry 18.

FIGS. 4(a) and 4(b) are diagrams illustrating a dose distribution in a depth direction, which is obtained when an irradiation object is irradiated with a particle beam.

FIG. 5 is a diagram illustrating a lateral dose distribution obtained when the irradiation object is irradiated with the particle beam.

DESCRIPTION OF EMBODIMENTS

Hereinafter, a particle beam therapy system including an MRI apparatus according to an embodiment will be described with reference to the drawings.
<Outline>
An outline of a particle beam therapy system according to an embodiment will be described with reference to FIGS. 1 to 3.

Figure 1:
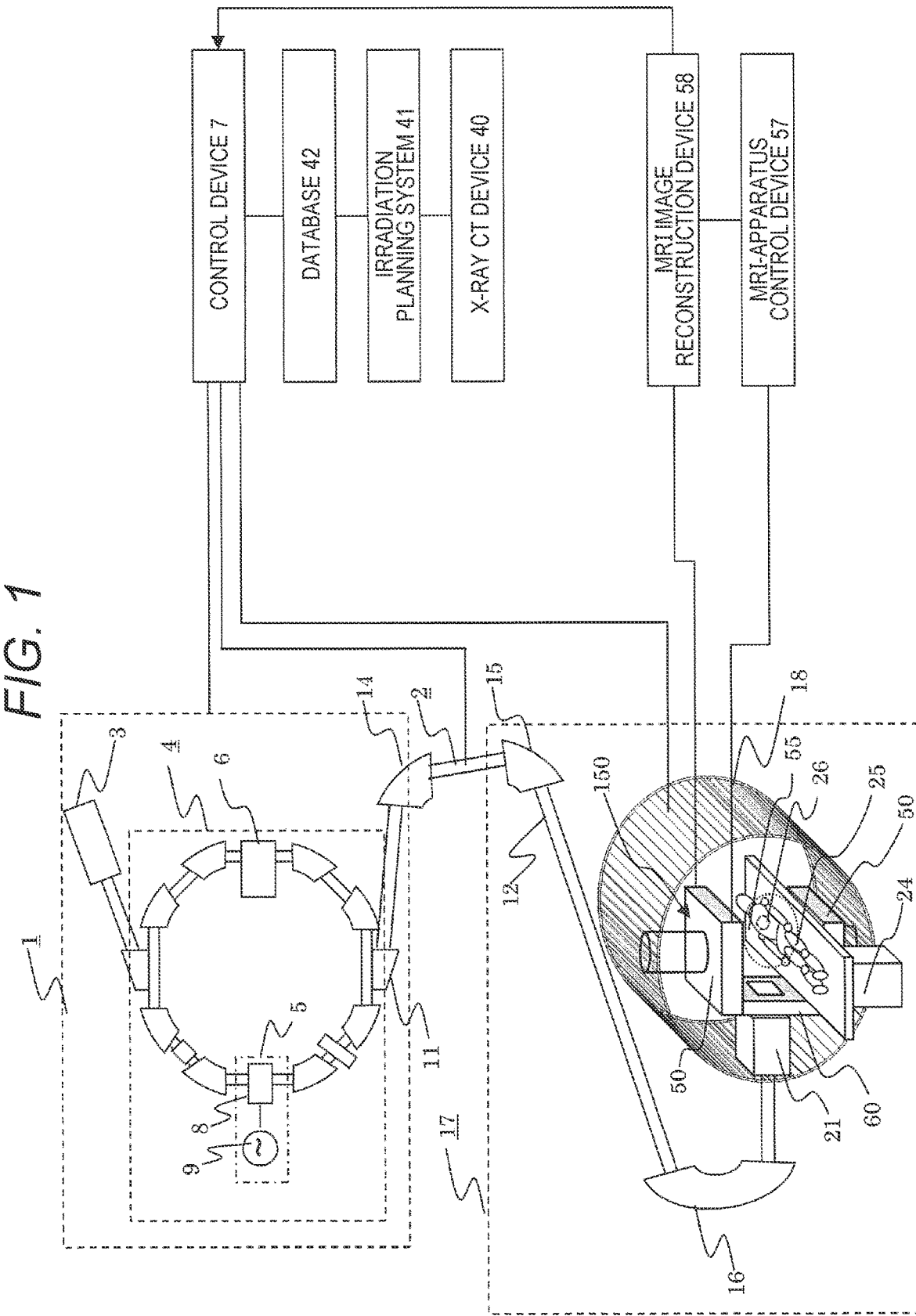
FIG. 1 is a block diagram illustrating an overall configuration of a particle beam irradiation system according to an embodiment.

As illustrated in FIG. 1, the particle beam therapy system in the embodiment includes at least a bed 24 on which an irradiation object (patient) 25 is mounted, an irradiation device 21 that irradiates an irradiation target 26 in the irradiation object 25 with a particle beam 20, and an MRI apparatus 150 that captures an image of the irradiation object 25.

The MRI apparatus 150 includes a static magnetic field generation device. The static magnetic field generation device includes a magnet 50 that generates a static magnetic field in an image capturing space 55 in which an irradiation target 26 is disposed, and a yoke 60, as illustrated in FIG. 2. The yoke 60 is made of a magnetic material and is disposed at a position outside from the image capturing space 55. With such an arrangement, the magnetic flux of the magnetic field generated by the magnet 50 passes through the yoke 60. In FIG. 1, as an example, the magnet 50 means a pair of magnets disposed with image capturing space 55 interposed therebetween, and the yoke 60 is disposed between the pair of magnets 50 and has a columnar shape connecting the pair of magnets 50.

The irradiation device 21 is disposed on the back surface side of the yoke 60 when viewed from the image capturing space 55, and irradiates the irradiation target 26 with the particle beam 20 from a through-hole 61 provided in the yoke 60 or a gap 62 (see FIG. 8) provided in the yoke 60.

The directions of the magnet 50 and the irradiation device 21 are set such that the direction in which the particle beam 20 having passed through the through-hole 61 or the gap enters the image capturing space 55 intersects with the direction of the static magnetic field 53 applied to the image capturing space 55 by the magnet.

Thus, the lines of magnetic force between the pair of magnets 50 pass through the yoke 60, and thus a leakage magnetic field is less likely to reach the irradiation device 21 disposed on the back surface of the yoke 60. In addition, since the axial direction of the particle beam 20 intersects with the direction of the static magnetic field 53, a leakage magnetic field leaking from the through-hole 61 or the gap 62 of the columnar yoke 60 is suppressed as compared with a case where the axial direction of the particle beam 20 coincides with the direction of the static magnetic field 53. Thus, since the irradiation device 21 is disposed in a space in which the leakage magnetic field of the magnet 50 is suppressed, the particle beam monitor 30 disposed on the central axis of the particle beam of the irradiation device 21 can be disposed close to the yoke 60, as illustrated in FIG. 3. Therefore, it is possible to suppress an influence of the magnetic field, and to measure the particle beam 20 by the particle beam monitor 30 with high accuracy. In addition, since the particle beam monitor 30 is close to the irradiation target 26, it is possible to suppress spread of the particle beam 20 at the time of reaching the irradiation target 26 due to scattering of the particle beam after passing through the particle beam monitor 30. Thus, it is possible to irradiate the irradiation target with the particle beam 20 having a small spot diameter.

The yoke 60 may be configured not to include the through-hole 61 or the gap 62. That is, the irradiation device 21 is disposed on the back surface side of the yoke 60 when viewed from the image capturing space 55, and irradiates the irradiation target 26 with the particle beam 20 from the side of the yoke 60 (see FIG. 9). The directions of the magnet 50 and the irradiation device 21 are set such that the direction in which the particle beam 20 having passed the side of the yoke 60 enters the image capturing space 55 intersects with the direction of the static magnetic field 53 applied to the image capturing space 55 by the magnet. Even in such a configuration, by disposing the irradiation device 21 on the back surface side of the yoke 60, a predetermined effect in that the leakage magnetic field is less likely to reach the irradiation device 21 can be obtained.

Embodiment 1

A particle beam therapy system in Embodiment 1 will be described in detail with reference to FIG. 1 and the like.

As illustrated in FIG. 1, the particle beam therapy system in the present embodiment includes a charged particle beam generation device 1, a beam transport system 2, a radiation therapy room 17, and a control device 7.

The charged particle beam generation device 1 includes an ion source, a linac 3 which is a pre-charged particle beam acceleration device, and a synchrotron 4. The synchrotron 4 includes a radio frequency application device 5 that is disposed in the orbit of the synchrotron 4 and applies radio frequency waves to charged particles, an acceleration device 6 that accelerates the charged particles, and an emission deflector 11. The radio frequency application device 5 includes a radio frequency applying electrode 8 and a radio-frequency applying power supply 9. The radio frequency applying electrode 8 is connected to the radio-frequency applying power supply 9 via a switch. The acceleration device 6 includes a radio frequency acceleration cavity disposed on an orbit of the particle beam and a radio frequency power supply that applies radio frequency power to the radio frequency acceleration cavity, and the acceleration device 6 accelerates the charged particles. The emission deflector 11 emits the accelerated charged particles from the synchrotron 4 and causes the accelerated charged particles to be incident to the beam transport system 2 connected to the emission deflector.

The beam transport system 2 includes a beam path 12, a quadrupole magnet, and bending magnets 14, 15, and 16. The beam path 12 is connected to the irradiation device 21 installed in the therapy room 17.

In the therapy room 17, a substantially tubular gantry 18 is installed. The gantry 18 is equipped with the bending magnets 15 and 16 which are a portion of the beam transport system 2, the irradiation device 21 that irradiates the irradiation target 26 with a charged particle beam, and the MRI apparatus 150.

The treatment bed 24 called a couch on which the irradiation object 25 is mounted is installed inside the gantry 18.

The gantry 18 is rotatable by a drive mechanism such as a motor (not illustrated). With the rotation of the gantry 18, the bending magnets 15 and 16, the irradiation device 21, and the MRI apparatus 150 mounted on the gantry rotate around the bed 24. As described above, the mounted devices rotate in conjunction with the rotation of the gantry 18, so that the irradiation object 25 can be irradiated with the particle beam from any direction in a plane perpendicular to the rotation axis of the gantry 18.

Figure 3:
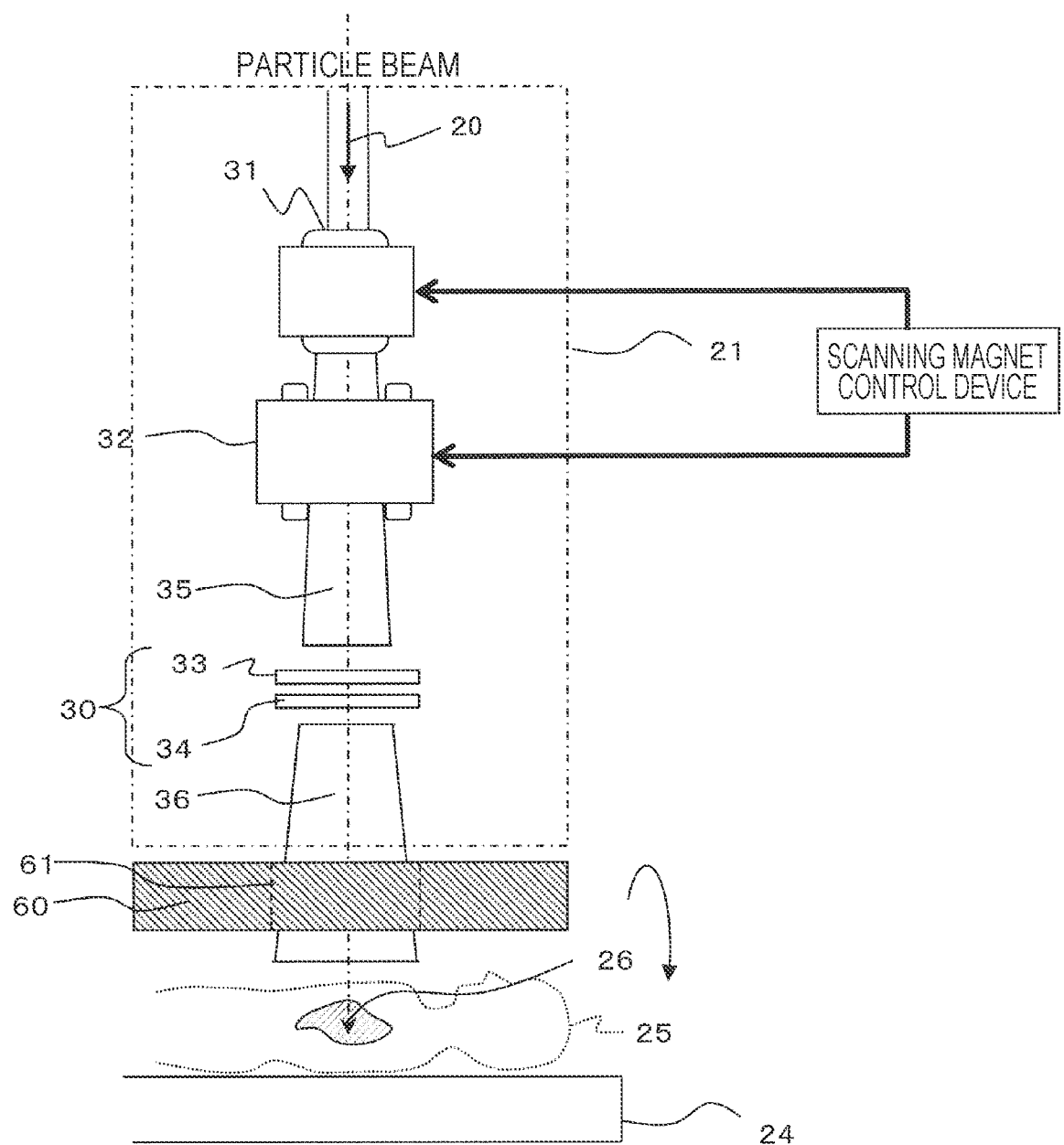
FIG. 3 is a block diagram illustrating a configuration of an irradiation device in the particle beam irradiation system in the embodiment.

As illustrated in FIG. 3, the irradiation device 21 has a configuration in which a vacuum chamber 35 provided with scanning magnets 31 and 32, a particle beam monitor 30, and a helium chamber 36 are arranged in order in a traveling direction of the particle beam 20 along the central axis of the particle beam 20.

Each of the two scanning magnets 31 and 32 deflects the particle beam in two directions (X direction, Y direction) in a plane perpendicular to the traveling direction of the particle beam 20. Thus, the irradiation position of the particle beam 20 on the irradiation target 26 is changed by the scanning magnets 31 and 32.

The particle beam monitor 30 includes a position monitor 34 and a dose monitor 33. The particle beam monitor includes a parallel plate electrode, and a voltage is applied to both sides of the electrode. When the particle beam passes through the particle beam monitor, the internal gas is ionized. The ionized electrons and ions move by an electric field and are collected at both electrodes. A structure in which a signal is collected by one electrode in the dose monitor 33, and the electrode is divided into a plurality of pieces in the position monitor is made. The position monitor 34 measures the position of the particle beam and the spread of the particle beam. The dose monitor 33 measures the amount of the particle beam with which irradiation is performed.

In order to concentrate the dose on the irradiation target 26, it is preferable to irradiate the irradiation target 26 with the particle beam 20 having a narrow beam diameter. However, when passing through the atmosphere or the structure, the particle beam 20 is scattered and the thickness increases. Therefore, it is preferable to reduce the amount of a substance on the passage path of the particle beam 20, and the vacuum chamber 35 is disposed in the irradiation device 21 so that the particle beam 20 passes through the vacuum immediately before the monitor.

The particle beam 20 passes through a vacuum window provided at an outlet of the vacuum chamber 35 and reaches the particle beam monitor 30. The particle beam monitor 30 is installed in the atmosphere in order to measure the position and amount of the beam by using an action of ionization of gas by the particle beam 20. The particle beam monitor 30 includes a thin film functioning as a monitor electrode.

The helium chamber 36 is disposed to reduce scattering of the particle beam 20 having passed through the particle beam monitor 30 due to the atmosphere, until the particle beam reaches the irradiation target 26. The helium chamber 36 is filled with helium. A vacuum chamber can be used instead of the helium chamber 36, but, since the particle beam 20 passes through the vacuum window in the vacuum chamber, the particle beam 20 is easily scattered due to the thickness of the vacuum chamber. In the present embodiment, it is possible to reduce the thickness of the window of the helium chamber 36 by using the helium chamber 36 having pressure equivalent to the atmospheric pressure. Thus, it is possible to reduce an occurrence of scattering of the particle beam 20 and to irradiate the irradiation target 26 with the thin particle beam 20.

In the present embodiment, as illustrated in FIG. 3, the yoke 60 of the MRI apparatus 150 is disposed between the irradiation target 26 and the particle beam monitor 30.

The MRI apparatus 150 will be described with reference to FIGS. 2(a) and 2(b). The magnet 50 has a configuration in which a coil 51 is wound in an annular groove provided in a surface on the image capturing space 55 side of a pair of disk-shaped magnetic poles 52 disposed with the image capturing space 55 interposed therebetween. The columnar yoke 60 is disposed at an end portion of the pair of magnetic poles 52. Thus, the passive shield type magnet 50 in which, by supplying a current to the coil 51, for example, a magnetic flux 53a directed from the magnetic pole 52 of the upper magnet 50 to the magnetic pole of the lower magnet 60 is generated, and a uniform static magnetic field 53 is formed in the image capturing space 55, and the magnetic flux 53a that has entered the magnetic pole 52 of the lower magnet 60 passes through the yoke 60 and returns to the magnetic pole 52 of the upper magnet 50 is configured. The yoke 60 is made of a magnetic material such as iron, and is also called a return yoke.

In the present embodiment, as illustrated in FIG. 2(a), the through-hole 61 through which the particle beam 20 passes is provided at the center of the yoke 60 in a width direction. The helium chamber 36 in the irradiation device 21 may be inserted into the through-hole 36 as illustrated in FIG. 3. The particle beam 20 passes through the helium chamber 36 and is applied from the window at the tip toward the irradiation target 26.

At this time, the directions in which the magnet 50 and the irradiation device 21 are mounted on the gantry 18 are set such that the magnetic field 53 generated by the magnet 50 intersects with (is perpendicular or substantially perpendicular to) the central axis of the particle beam 20.

Although not illustrated in FIGS. 2(a) and 2(b), a gradient magnetic field coil, a transmission coil, and a reception coil are disposed on the image capturing space 55 side of the magnet 50. The gradient magnetic field coil applies gradient magnetic fields in three directions in the image capturing space 55. The transmission coil excites nuclear magnetism by irradiating the irradiation object 25 with radio frequency waves. The reception coil receives a nuclear magnetic resonance signal (NMR signal) generated from the irradiation object 25. Thus, phase information indicating positions in the three directions is added to the NMR signal received by the reception coil in accordance with the magnitude of the gradient magnetic field.

The irradiation object 25 is disposed by the bed 24 so as to enter the image capturing space 55 of the MRI apparatus 150.

Although the magnet 50 is configured to include the coil 51 in FIG. 3, the generation source of the magnetic flux 53a is not necessarily limited to the coil 51. For example, a permanent magnet can be used as the magnet 50. A superconducting coil may be used as the coil 51. In this case, a configuration in which the superconducting coil 51 is cooled by bringing a cryostat into contact with each of the upper and lower magnetic poles 52 may be made. The pair of magnets 50 and the yoke may be covered with a vacuum vessel for heat insulation.

Next, a control system 7 in the particle beam irradiation system in the present embodiment will be described with reference to FIG. 1. The control system 7 is connected to a database 42 which is a storage device. The database 42 is connected to an irradiation planning system 41 connected to an X-ray CT device 40. Using an image of the irradiation object 25 captured by the X-ray CT, the beam diameter of the particle beam 20, and the like, the irradiation planning system 41 creates an irradiation plan for defining which position of the irradiation target 26 is irradiated with how much dose, and stores the irradiation plan in the database 42. The control device 7 reads the irradiation plan and sequentially performs irradiation with the particle beam 20 in accordance with the plan. Therefore, the control device 7 is connected to and controls the charged particle beam generation device 1, the beam transport system 2, the gantry 18, a scanning magnet power supply that excites the scanning magnets 31 and 32, each monitor in the irradiation device 21, and each unit of the MRI apparatus.

An MRI-apparatus control device 57 is connected to each unit of the MRI apparatus 150. The MRI-apparatus control device 57 causes each unit of the MRI apparatus 150 to execute a predetermined pulse sequence in accordance with an instruction from the control device 7 to execute capturing of an MRI image. Specifically, an irradiation object in the image capturing space is irradiated with a radio-frequency pulse from the transmission coil to excite nuclear magnetism, and a nuclear magnetic resonance signal is collected by the reception coil while a gradient magnetic field is applied from the gradient magnetic field coil. The obtained nuclear magnetic resonance signal is transmitted from the receiving coil to an MRI image reconstruction device to reconstruct the image.

The relation between the depth of the irradiation target 26 and the energy of the particle beam 20 to be irradiated when the surface of the irradiation object 25 is set as a reference will be described with reference to FIGS. 4 and 5. FIG. 4 is a diagram in which the horizontal axis indicates the depth of the irradiation target 26 and the vertical axis indicates the dose of the particle beam. As illustrated in FIG. 5, the irradiation planning system 41 determines the position and the energy of the particle beam 20 to be irradiated so that irradiation with the particle beam 20 is performed, and thereby the entire irradiation target 26 is irradiated with a particle beam of a dose equal to or more than a predetermined value. Here, in the case of treatment of cancer or the like, the irradiation object 25 is a person, and the irradiation target 26 is a tumor.

FIG. 4(a) illustrates the dose distribution formed in the irradiation object by the single-energy particle beam, as a function of the depth. The peak in FIG. 4(a) is referred to as a Bragg peak. The position of the Bragg peak depends on the energy of the particle beam. Therefore, by adjusting the energy of the particle beam 20, it is possible to adjust the position of the Bragg peak and to perform irradiation with the particle beam of an appropriate dose to a desired depth of the irradiation target 26. The irradiation target 26 has a thickness in the depth direction, but the Bragg peak is a sharp peak. Thus, it is possible to form a uniform high dose region (SOBP) having the same thickness as the irradiation target 26 in the depth direction in a manner that the particle beam having several energies as illustrated in FIG. 4(b) is sequentially irradiated at an appropriate intensity ratio, and the Bragg peaks are superimposed.

The relation between the lateral spread of the irradiation target 26 in a direction perpendicular to the beam axis (the direction of an XY plane) and the particle beam will be further described with reference to FIG. 5. In FIG. 5, the horizontal axis indicates the spread of the irradiation target 26 in the horizontal direction, and the vertical axis indicates the dose at an irradiation spot. A direction perpendicular to the beam axis is referred to as a lateral direction. After reaching the irradiation device 21, the particle beam 20 can be scanned in two directions by the two scanning magnets 31 and 32 installed perpendicular to each other. Thus, the particle beam 20 can reach a desired position in the lateral direction. The spread of the particle beam in the lateral direction can be approximated by a Gaussian distribution shape. By arranging the Gaussian distributions at equal intervals and setting the distance between the Gaussian distributions to be about the standard deviation of the Gaussian distribution, the added distribution has a uniform region. The dose distribution in the form of a Gaussian distribution arranged in this manner is referred to as a spot. By scanning the particle beam and arranging a plurality of spots at equal intervals, it is possible to form a uniform dose distribution in the lateral direction. Thus, it is possible to move the Bragg peak in the depth direction by the beam scanning in the lateral direction by the scanning magnets 31 and 32 and the change of the beam energy of the particle beam 20 emitted from the synchrotron 4 and to form a uniform irradiation field. A unit of an irradiation field in which irradiation is performed with the same energy and which spreads in the lateral direction by scanning of the particle beam by the scanning magnet is referred to as a slice.

The irradiation planning system 41 determines an irradiation parameter, a gantry angle, and irradiation object position information necessary for irradiation before irradiating the irradiation target 26 with the particle beam. The irradiation parameter includes the number of slices N and N pieces of slice data. The slice represents a set of spots irradiated with the same energy. The slice data includes a slice number i, energy Ei, the number of spots Ni, and Ni pieces of spot data. The spot data includes a spot number j, an irradiation position (Xij, Yij), and a target dose Dij. A procedure in which the irradiation planning system 41 creates an irradiation plan including the irradiation parameters will be described below.

The irradiation object 25 is photographed in advance by the X-ray CT device 40. The X-ray CT device 40 has a function of creating a CT image for each phase of the movement when the irradiation target 26 periodically moves. In particular, when a patient is photographed, a CT image for each respiratory phase can be acquired. The X-ray CT device 40 photographs the irradiation object, and creates CT images of the irradiation object 25 for n phases. The X-ray CT device 40 transmits the created CT image to the irradiation planning system 41.

The irradiation planning system 41 displays the received image data on a screen of a display device (not illustrated). An operator selects a CT image having a reference phase from the CT images for the respective phases. For example, when the movement of an affected area by respiration is considered, an expiratory phase is selected.

The operator designates a region desired to be the irradiation target 26 on the selected CT image. The irradiation planning system 41 obtains and determines an installation position, a gantry angle, and irradiation parameters of the irradiation object, which can cause a dose distribution to be formed in a designated area. That is, the irradiation planning system 41 determines an irradiation object installation position and a gantry irradiation angle based on irradiation object information input by the operator, and then divides the irradiation target 26 (affected area) into a plurality of slices in the depth direction and determines the required number of slices N. The irradiation planning system 41 obtains the energy Ei of the particle beam suitable for irradiation for each depth of each slice (slice number i).

The irradiation planning system 41 further determines the number Ni of irradiation spots irradiated with the particle beam 20, the spot number j, the irradiation position (Xij, Yij) of each spot, and the target dose Dij of each spot, in accordance with the shape of each slice. Since the particle beam 20 bends by the influence of the magnetic field generated by the MRI apparatus, the above parameters are determined in consideration of the influence.

The irradiation planning system 41 calculates a dose distribution when the irradiation object is irradiated with the determined values, in consideration of the magnetic field of the MRI apparatus, and displays the obtained dose distribution on the display device.

The data created in this manner is created by the number of gantry angles. The created irradiation parameter, gantry angle, and irradiation object position information are transmitted to the database 42 and recorded in the database 42 as an irradiation plan.

Figure 6:
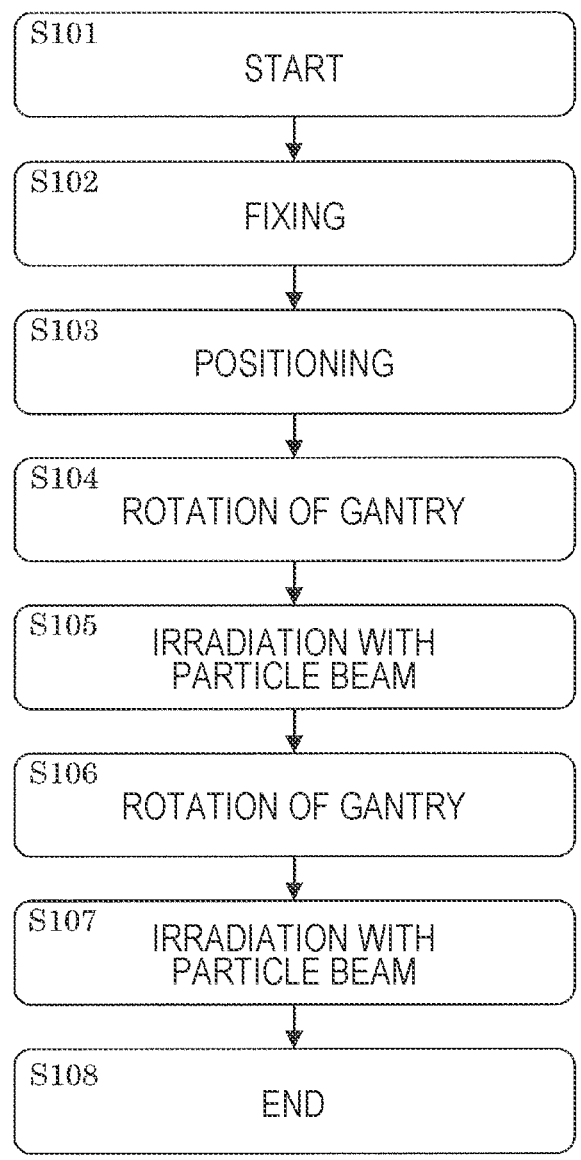
FIG. 6 is a flowchart illustrating a procedure of irradiating an irradiation object with a particle beam in Embodiment 1.

A procedure of forming a desired dose distribution by irradiating the irradiation target 26 (when the irradiation object 25 is a patient), which is an affected area, with the particle beam 20 by using the irradiation parameter, the irradiation object installation information, and the gantry angle created by the above procedure will be described with reference to FIG. 6. FIG. 6 illustrates an example in which irradiation with the particle beam is performed from two directions.

In S101, a patient enters the therapy room and starts a series of treatments.

In S102, the patient is fixed on the bed 24 by the operator. Specifically, the operator fixes the patient to the bed 24 outside the gantry 18, and then moves the bed 24 into the gantry 18.

In S103, the control device 7 instructs the MRI-apparatus control device 57 to perform image capturing, and further causes the MRI image reconstruction device 58 to reconstruct an image, acquire an MRI image, and perform positioning of the irradiation target 26. In the positioning, the obtained MRI image is compared with the image of the irradiation object installation information recorded in the database 42, and the bed 24 is moved so that the patient is installed at the planned position.

In S104, the control device 7 rotates the gantry to match with a direction in which the particle beam is first irradiated.

In S105, the control device 7 performs irradiation with the particle beam. The irradiation flow with the particle beam will be described later.

When the irradiation with the particle beam is completed, the control device 7 changes the irradiation direction in the next S106, and performs irradiation with the particle beam again in S107.

When the irradiation with the particle beam is completed, the operator pulls out the bed 24 from the gantry in S108. The patient gets off the couch and leaves the therapy room.

During the series of treatments, the magnet 50 of the MRI apparatus is in a state where the magnetic field is normally excited, but, an operation in which the magnetic field is excited only when the image, as will be described later, is acquired is possible.

Figure 7:
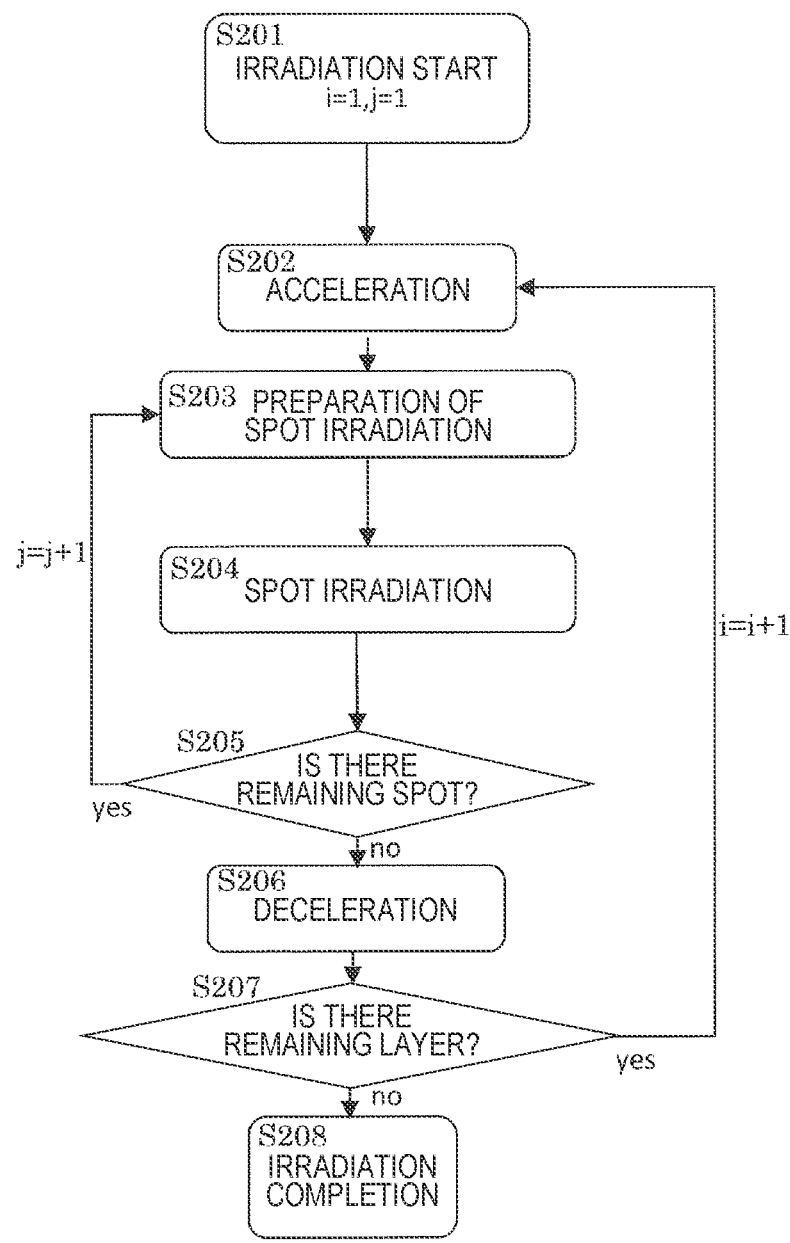
FIG. 7 is a flowchart illustrating a procedure in which the particle beam irradiation system performs irradiation with a particle beam.

Next, the irradiation with the particle beam by the control device 7 in S105 and S107 will be described with reference to FIG. 7.

When the operator presses an irradiation preparation start button on a console connected to the control device 7, the control device 7 receives irradiation object installation information from the database 42, and prepares an excitation pattern of each electromagnet of the synchrotron 4 to emit a charged particle beam having the designated energy. In addition, the control device 7 sets the irradiation parameter from the database 42, and sets the excitation current value obtained from the irradiation position and the energy, in the power supply of the scanning magnets 31 and 32.

In Step 201, the control device 7 starts irradiation from a spot of the particle beam 20 having the energy number i=1 and the spot number j=1. The control device 7 controls the synchrotron 4 to accelerate the particle beam to the energy E1 of the energy number i=1 and emit the particle beam.

The control device 7 instructs the MRI-apparatus speech device 57 to capture MRI images at a constant cycle and instructs the MRI image reconstruction device 58 to perform image reconstruction.

The control device 7 calculates the position (target coordinates) of the irradiation target 26 from the acquired MRI image.

In Step 202, the synchrotron 4 starts accelerating. The control device 7 controls the ion source, the linac 3, and the synchrotron 4 to accelerate the particle beam 20. The particle beam generated in the ion source is accelerated by the linac 3 and is incident on the synchrotron 4. The incident particle beam is applied with a radio frequency from the acceleration device 6 and accelerated to the energy E1 for irradiation with the first slice number.

In Step 203, the control device 7 prepares irradiation of a spot of the particle beam 20. The control device 7 controls the power supply of the scanning magnets 31 and 32 to excite the scanning magnets 31 and 32 so as to correspond to the irradiation positions of i=1 and j=1. Then, the control device 7 receives the MRI image and determines whether the target position in the image coincides with or approaches the position when the irradiation planning system 41 creates the irradiation parameters. When the target position coincides with or approaches such a position, the control device starts the irradiation of the particle beam in S204.

In Step 204, the control device 7 controls the radio frequency application device 5 to apply a radio frequency to the particle beam 20. The particle beam 20 to which the radio frequency is applied passes through the emission deflector 11, passes through the beam path 2, and reaches the irradiation device 21 in the therapy room 17. The particle beam 20 is scanned by the scanning magnets 31 and 32 in the irradiation device 21, passes through the position monitor 34 and the dose monitor 33, reaches the inside of the irradiation object, and is applied to the irradiation target 26.

The dose of the particle beam 20 reaching the irradiation target 26 is detected by the dose monitor 33. The control device 7 compares the count of the signal from the dose monitor 33 with the target dose of i=1 and j=1 described in the irradiation parameter. When the count reaches the target dose, the control device starts stopping of the emission. The control device 7 controls the radio frequency application device 5 to stop the application of the radio frequency and stop the emission. The control device checks that the difference between the position measured by the position monitor and the position described in the irradiation parameter is equal to or less than a threshold set in advance.

In Step 205, when there is a spot of the same slice whose irradiation has not been completed, that is, when the spot number j satisfies j<Ni, the process returns to Step 203 in order to irradiate the (j+1)th spot. When all the spots of the same slice have been irradiated, that is, when j=Ni, the process proceeds to Step 206.

In Step 206, the control device decelerates the particle beam and turns into a state where a new particle beam can be incident from the linac.

In Step 207, when there is a layer whose irradiation is not completed, that is, when i<N, the process proceeds to Step 202 in order to irradiate the (i+1)th layer. When the irradiation of all the layers is completed, that is, when i=N, the process proceeds to Step 208, and the irradiation is completed.

By irradiating the irradiation target 26 with the particle beam 20 with the above procedure, it is possible to irradiate the irradiation target 26 with the particle beam 20 in accordance with the irradiation plan.

The particle beam monitor 30 includes the parallel plate electrode, and a voltage is applied to both sides of the electrode. When the particle beam passes through the particle beam monitor, the internal gas is ionized. The ionized electrons and ions move by an electric field and are collected at both electrodes.

Regarding the particle beam monitor 30, the dose monitor 33 collects signals by one electrode, and the position monitor 34 collects a signal for each of the plurality of divided electrodes. When the particle beam monitors 30 are installed in the magnetic field, the ionized electrons and ions are influenced by the magnetic field and the path to the electrode changes. Thus, correction accompanying the path change is required. Alternatively, there is a possibility that it is not possible to collect electrons and ions by the electrode. With the configuration as in the present embodiment, it is possible to reduce the magnetic field intensity around the MRI and to install the particle beam monitor near the patient. As the measurement is performed closer to the patient, it is possible to measure the position and amount of the particle beam reaching the patient with higher accuracy.

As described above, according to the configuration in Embodiment 1, it is possible to irradiate a wide region with a thin particle beam while the wide region is imaged by MRI. In addition, since a wide region can be imaged by MRI, it is possible to image the entire region from the position at which the particle beam is incident on the body to the target. Since all the paths of the particle beam in the patient body can be imaged, the MRI image can be used singly or in combination with the X-ray CT image captured in treatment planning, and thus be used to calculate the dose distribution. Thus, the present embodiment can also be applied to dose simulation before or after irradiation, and adaptive irradiation that optimizes the irradiation position and amount immediately before treatment. In addition, since a wide area can be irradiated, it is possible to irradiate the entirety of the target without moving the patient for a large target or a long target.

By photographing the target during particle beam irradiation using the MRI image, not only the position but also the shape of the target can be measured. Since the change in shape can be measured, it is possible to perform irradiation with the particle beam with high accuracy.

In the present embodiment, since the particle beam monitor 30 can be disposed at a position close to the irradiation target 26, it is possible to suppress the spread of the beam diameter of the particle beam 20 and to irradiate the irradiation target 26 with the particle beam 20 of a small spot. Thus, it is possible to cause the dose to concentrate on the irradiation target 26.

In the present embodiment, it is not necessary to form a through-hole in the magnetic pole 52, and the through-hole 61 of the return yoke 60 is passed, so that it is possible to achieve both a large MRI field and a large irradiation field of a particle beam.

Although FIG. 3 illustrates a configuration in which the tip of the helium chamber 36 is inserted into the through-hole 61 of the yoke 60, the tip of the helium chamber 36 may be retracted outward from the through-hole 61. For example, the helium chamber 36 is made to have a bellows structure, and thus the helium chamber 36 can be inserted into the through-hole 61 or retracted outward.

Embodiment 2

A particle beam therapy system including an MRI apparatus according to Embodiment 2 will be described.

Figure 8:
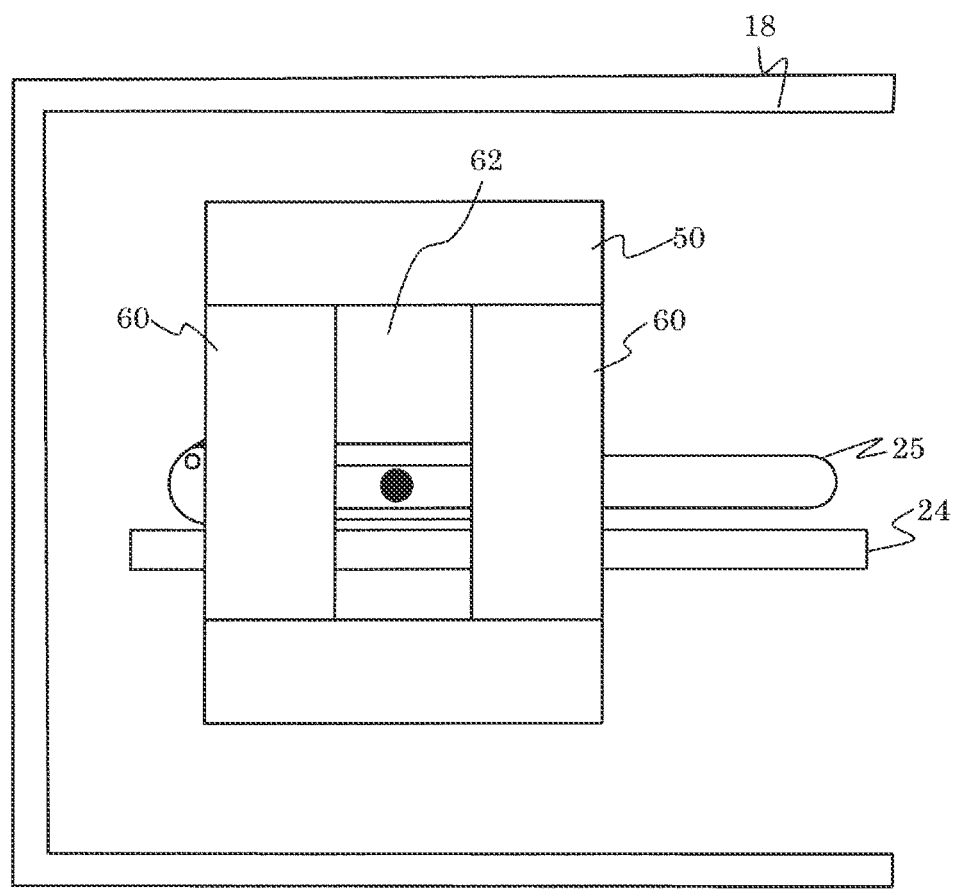
FIG. 8 is a cross-sectional view illustrating an arrangement example of two columnar return yokes in Embodiment 2.
Figure 9:
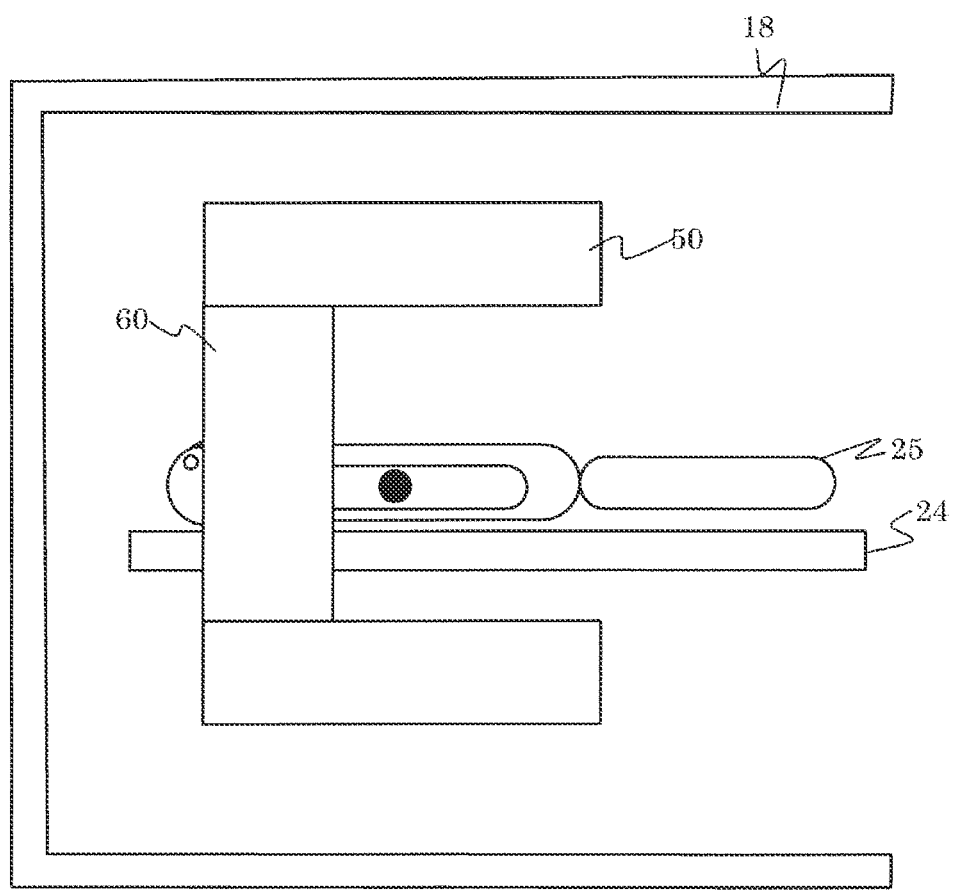
FIG. 9 is a cross-sectional view illustrating an arrangement example of one return yoke in Embodiment 2.

The return yoke 60 in the MRI apparatus has one columnar shape in Embodiment 1, but may have two columnar shapes as illustrated in FIG. 8 or a columnar shape without a through-hole as illustrated in FIG. 9.

As illustrated in FIG. 8, when two columnar return yokes 60 are used, irradiation with the particle beam 20 can be performed from the gap 62 between the two yokes 60 without forming the through-hole 61.

The gap 62 is not limited to the configuration of being formed between the two yokes 60, and a slit-like gap 62 may be provided in one yoke 60.

As illustrated in FIG. 9, in the case of one yoke 60, the through-hole 61 may not be provided, and the irradiation device 21 may irradiate the image capturing space 55 with the particle beam 20 from the side of the column 60. Also in this case, by disposing the irradiation device 21 on the back surface side of the yoke 60, a predetermined effect in that the leakage magnetic field is less likely to reach the irradiation device 21 can be obtained.

Other components are similar to those in Embodiment 1.

Embodiment 3

A particle beam therapy system including an MRI apparatus according to Embodiment 3 will be described.

Figure 10:
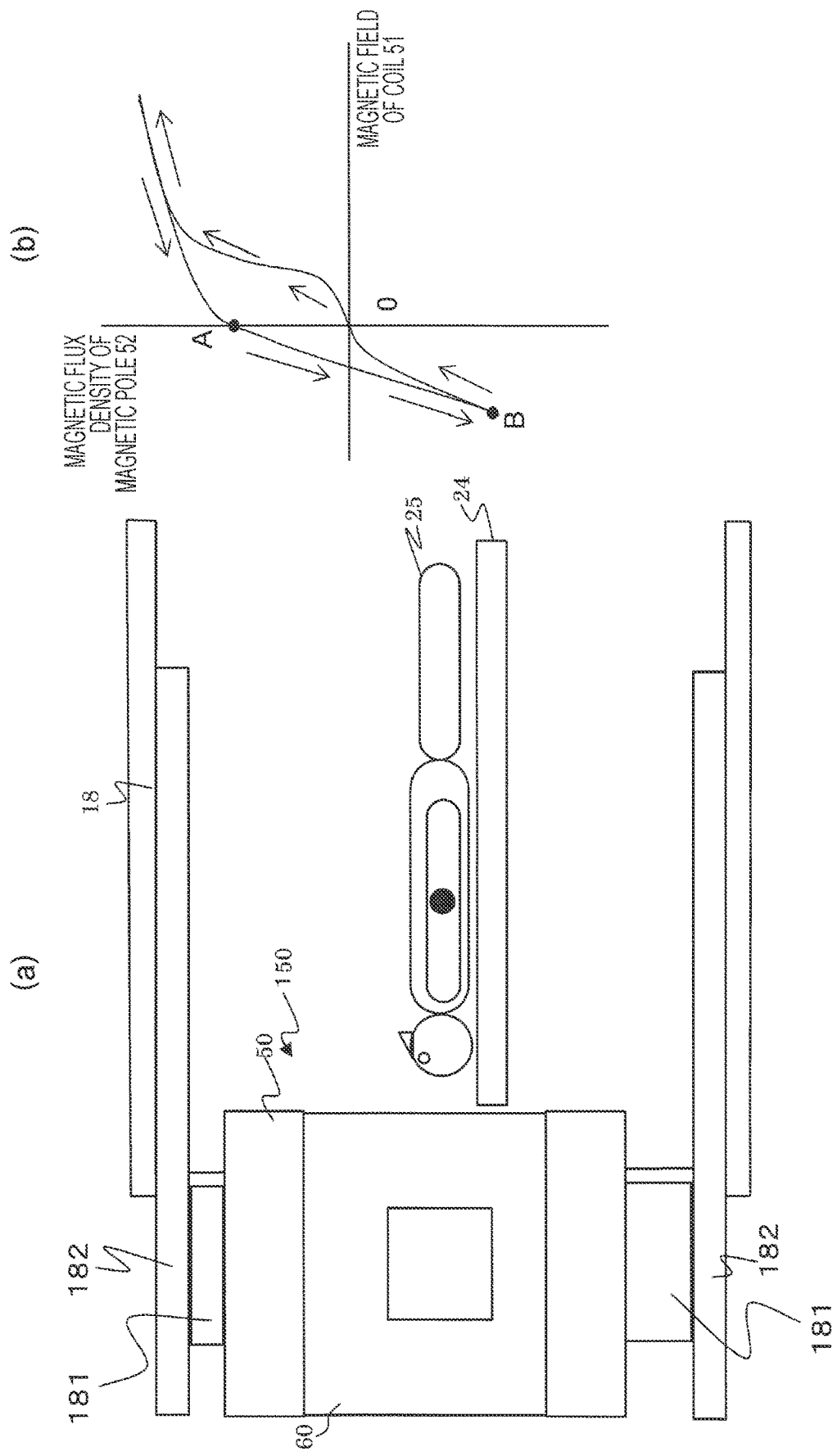
FIG. 10(a) is a cross-sectional view of a plane parallel to a rotation axis direction of a gantry, which illustrates a configuration for transporting an MRI apparatus in Embodiment 3.
FIG. 10(b) is a graph illustrating residual magnetic flux density during demagnetization.

In Embodiment 3, as illustrated in FIG. 10(a), the magnetic field of the magnet 50 in the MRI apparatus 150 is demagnetized to retract the MRI apparatus 150.

That is, the rotary gantry 18 includes a support mechanism 181 that detachably supports the MRI apparatus 150, and a transport mechanism (rail) 182 that moves the MRI apparatus removed from the rotary gantry 18 in a direction separated from the bed 24. The direction in which the transport mechanism 182 transports the MRI apparatus 150 is the axial direction of the rotary gantry 18.

As described above, there is an advantage that the irradiation field of the particle beam 20 is widened by retracting the MRI apparatus 150. In addition, it is possible to perform irradiation with the particle beam 20 by changing the angle of the bed 24, and to irradiate the irradiation target 26 of the irradiation object 25 with the particle beam 20 from a desired direction.

The MRI apparatus 150 may be retracted together with the helium chamber 36, or only the MRI apparatus 150 may be transported (retracted) alone after the helium chamber 36 is retracted in a beam axial direction of the particle beam. At this time, the helium chamber 36 is contracted by providing an expansion/contraction mechanism such as a bellows in the helium chamber 36, so that only the tip of the helium chamber 36 may be removed from the through-hole 61 without retracting the entirety of the helium chamber 36, and the MRI apparatus 150 may be transported (retracted) alone.

When the magnet 50 is demagnetized, the current (or permanent current) flowing through the coil 51 of the magnet 50 may be stopped. At this time, as indicated by a point A in FIG. 10(b), even though the current of the coil 51 is cut off and the generated magnetic field is set to 0, a residual magnetic field (residual magnetic flux density) is generated in the magnetic pole 52 and the yoke 60 and does not become 0. Therefore, the residual magnetic field (residual magnetic flux density) can be set to 0 in the magnetic pole 52 and the yoke 60 in a manner that, after the current flowing through the coil 51 is reduced to 0, the reverse current flows through the coil 51 (point B), and the current is gradually brought close to 0. Thus, the magnet 50 can be demagnetized and transported by the transport mechanism 182.

Embodiment 4

A particle beam therapy system including an MRI apparatus according to Embodiment 4 will be described.

Figure 11:
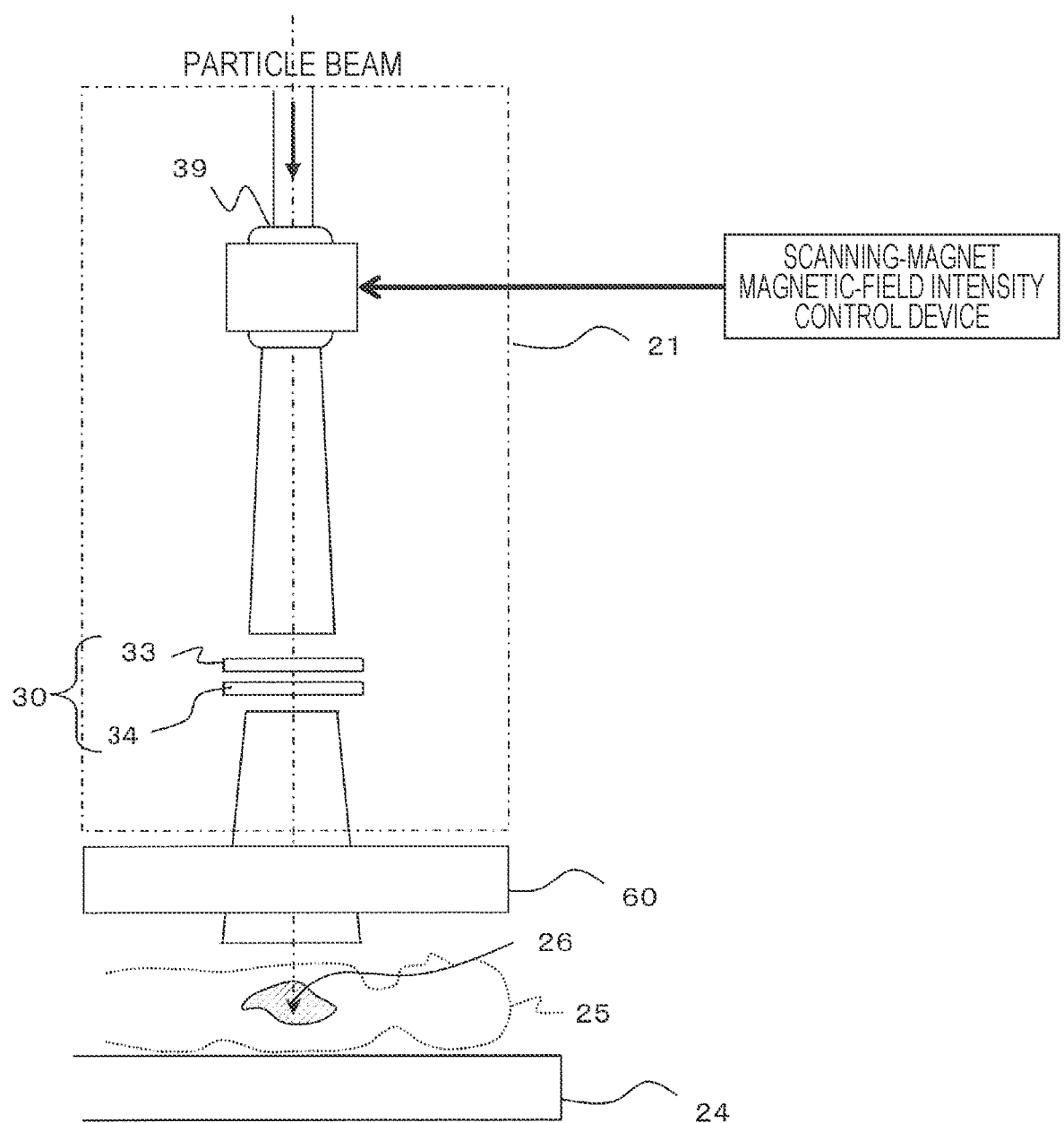
FIG. 11 is a block diagram illustrating a configuration of an irradiation device in a particle beam irradiation system in Embodiment 4.

As illustrated in FIG. 11, the MRI apparatus in Embodiment 4 uses an integrated scanning magnet 39 capable of scanning in two directions as one magnet for scanning the particle beam 20 in two directions. In such an integrated scanning magnet 39, since the length of the particle beam 20 in the axial direction is short, it is possible to reduce the distance from the irradiation target 26 to the scanning magnet 39 while securing the distance between the scanning magnet 39 and the particle beam monitor 30 and the distance between the particle beam monitor 30 and the yoke 60 of the MRI apparatus 150.

As described above, by reducing the distance from the target 26 to the scanning magnet 39, it is possible to reduce the distance from the outlet of the bending magnet 16 closest to the irradiation device in the beam transport system 2 to the target 26. Thus, since the gantry 18 can be configured to be small, it is possible to downsize the apparatus.

Such an integrated scanning magnet 39 has a known configuration (see JP 2016-083344 A and U.S. Pat. No. 8,378,312), and thus a detailed description thereof will be omitted.

Embodiment 5

A particle beam therapy system including an MRI apparatus according to Embodiment 5 will be described.

Figure 12:
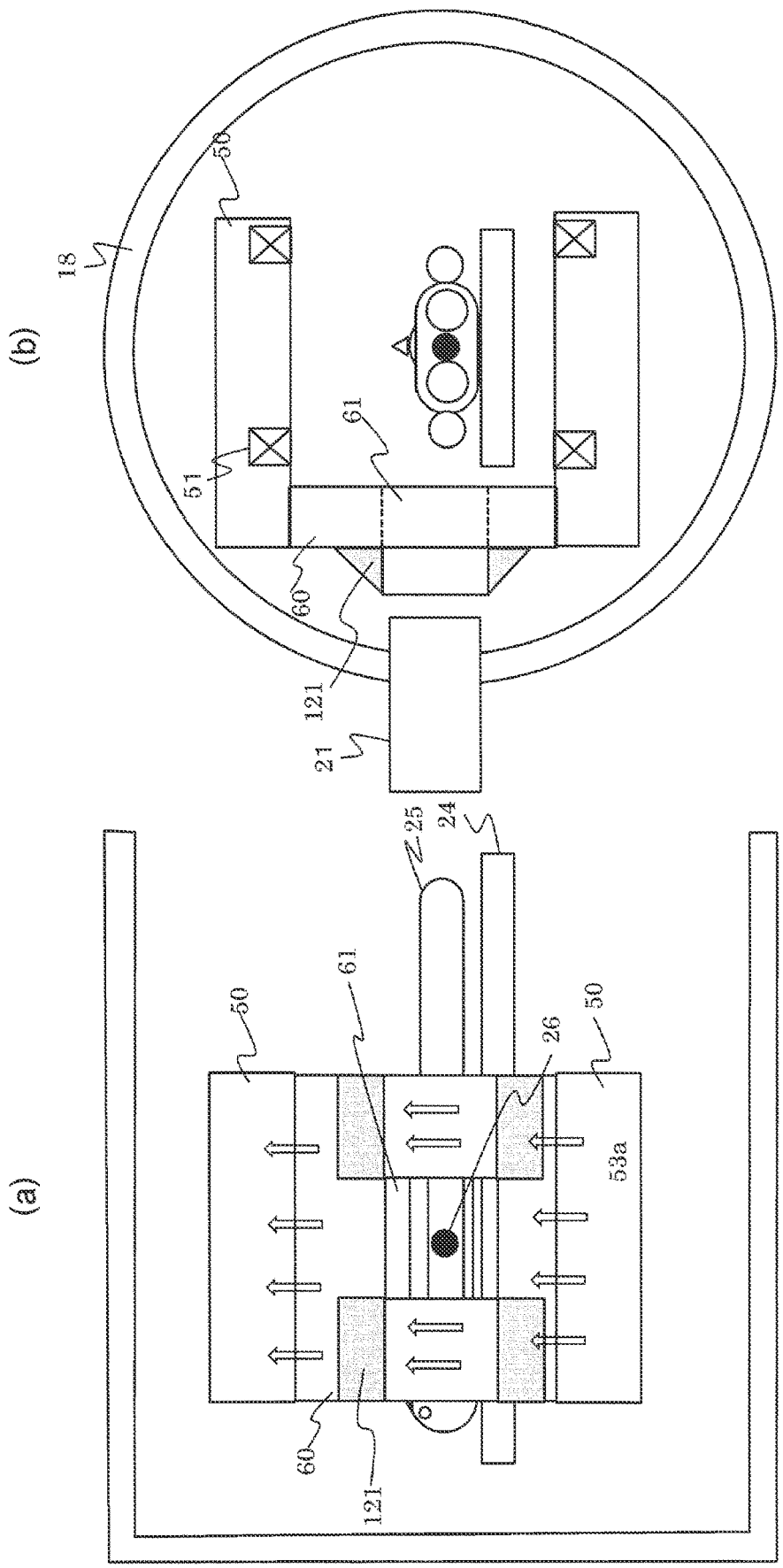
FIG. 12(a) is a cross-sectional view of a plane parallel to a rotation axis direction, which illustrates arrangement of a rotary gantry 18, a magnet 50, and a yoke 60 in a particle beam irradiation system in Embodiment 5.
FIG. 12(b) is a front view of the rotary gantry 18.

As illustrated in FIG. 12, in the particle beam therapy system in Embodiment 5, the through-hole 61 is provided at the center in the width direction of the columnar yoke 60 similarly to the particle beam therapy system in Embodiment 1. A protrusion 121 having a larger width or depth than a width or a depth of a portion at which the through-hole 61 is not disposed is provided on both sides of the through-hole 61 of the yoke 60.

By providing the protrusion 121, it is possible to reduce the magnetic resistance of the yoke 60 on both sides of the through-hole 61. Thus, the magnetic flux more easily flows through the yoke 60 than a case where the protrusion 121 is not provided, and it is possible to further reduce the leakage magnetic field as compared with Embodiment 1.

Embodiment 6

Figure 13:
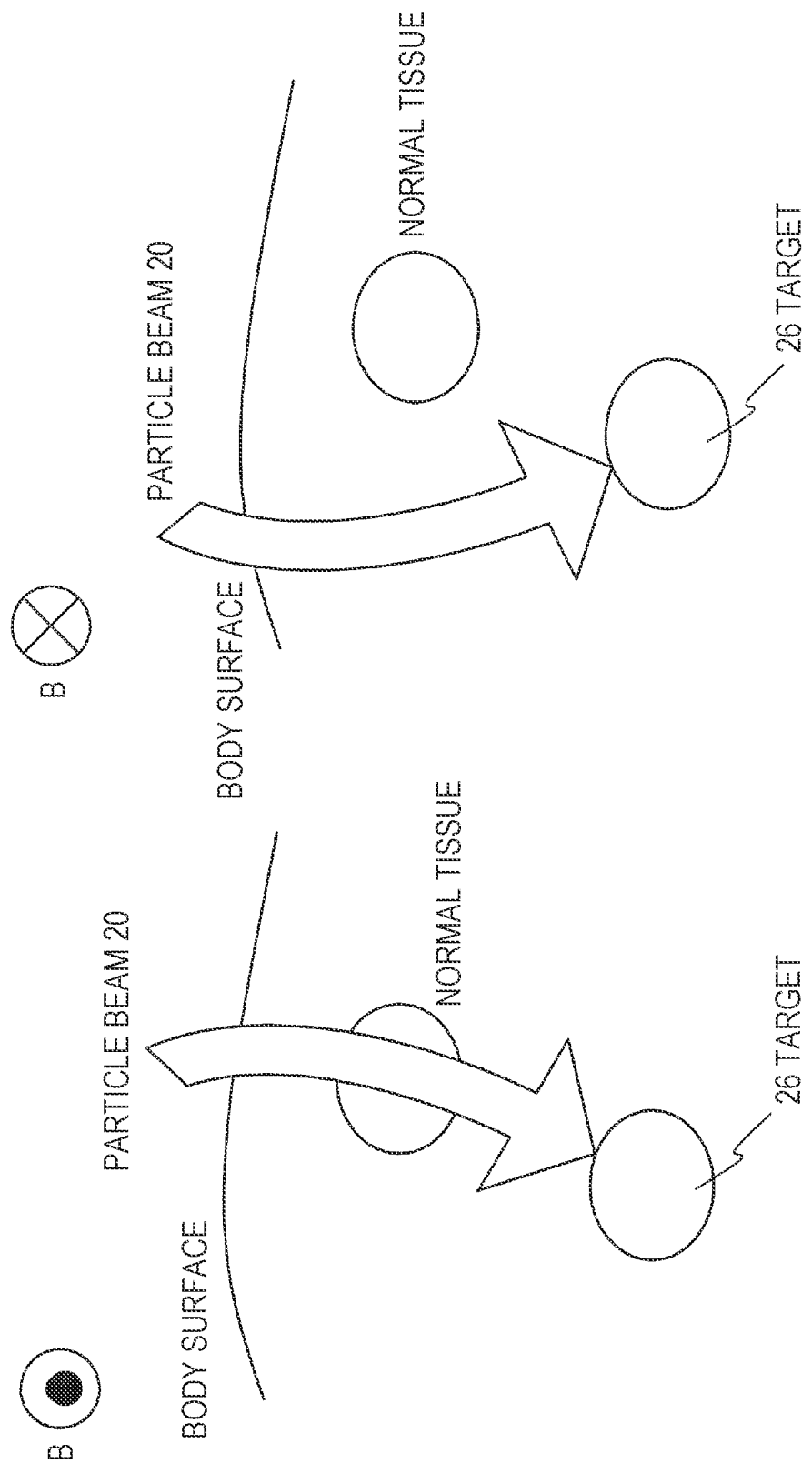
FIG. 13 is an explanatory diagram illustrating an example in which a direction of curvature of the particle beam is reversed by reversing a magnetic field in Embodiment 6.

A particle beam therapy system including an MRI apparatus according to Embodiment 6 will be described with reference to FIG. 13.

In the present embodiment, the current flowing through the coil 51 that excites the magnetic pole 52 of the magnet 50 in the MRI apparatus 150 is reversed depending on the position of the target 26. Thus, as illustrated in FIG. 13, the direction of the curvature of the particle beam 20 can be reversed.

Thus, when there is a normal tissue of which the irradiation dose is desired to be lowered around the target 26, the direction of the magnetic field of the magnet 50 is determined so that the particle beam curves to avoid the tissue. Thus, it is possible to lower the dose of the normal tissue of which the irradiation dose is desired to be lowered.

Embodiment 7

A particle beam therapy system including an MRI apparatus according to Embodiment 7 will be described with reference to FIG. 14.

In the particle beam therapy system in Embodiment 7, the magnet 50 has a cylindrical shape, and the image capturing space 55 is formed inside the cylindrical magnet 50. In this case, the yoke 60 is disposed on an outer surface of the cylindrical magnet 50. A second through-hole 151 is provided at a position at which the through-hole 61 of the yoke 60 is provided, so as to overlap the through-hole 60 in the cylindrical magnet 50. The particle beam 20 passes through the first and second through-holes 61 and 151 and is applied to the irradiation target 26 in the image capturing space 55.

As described above, it is possible to reduce the leakage magnetic field on the outer peripheral side of the magnet 50 by disposing the yoke 60 on the outer peripheral surface even though the magnet 50 has a cylindrical shape. Thus, by disposing the irradiation device 21 at the position of the yoke 60 as in FIG. 3, the particle beam monitor 30 can be disposed close to the MRI apparatus 150.

Figure 14:
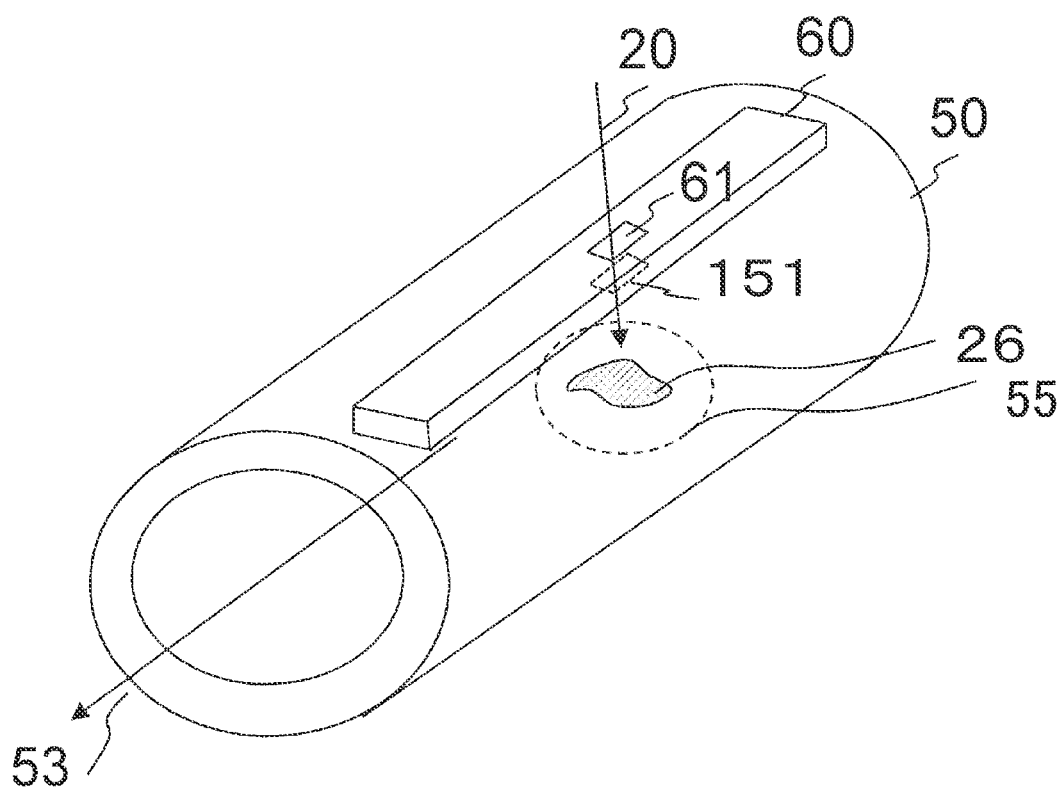
FIG. 14 is a perspective view of a magnet 50 and a yoke 60 in a particle beam therapy system in Embodiment 7.

Although FIG. 14 illustrates the case where the yoke 60 is columnar, even when the yoke 60 is cylindrical and disposed to cover the entirety of the cylindrical magnet 50, it is possible to more effectively reduce the leakage magnetic field to the outer peripheral side the configuration in FIG. 14.

When the yoke 60 is disposed outside the cylindrical magnet 50, it is possible to prevent generation of the leakage magnetic field, so that it is possible to improve the strength and the uniformity of the static magnetic field in the image capturing space 55 as compared to the configuration in which the yoke 60 is not disposed.

Modification Example 1

In each of the embodiments described above, an example in which the synchrotron 4 is used as an accelerator that accelerates charged particles has been described, but a cyclotron can be used.

In Embodiment 1, the spot scanning in which the emission of the particle beam 20 is stopped for each spot has been described as an example, but the present invention can also be applied to raster scanning and line scanning in which the emission of the particle beam is not stopped.

In Embodiment 1, the gate irradiation in which irradiation with the particle beam is performed only when the target comes to the target position has been described, but tracking irradiation in which the excitation amount of the scanning magnet is changed in accordance with the target position can also be performed. The gate irradiation and the tracking irradiation can be combined.

Modification Example 2

Considering the influence of bending of the particle beam by the magnetic field, it is effective to adjust the angle of the particle beam incident on the irradiation device, the position of the scanning magnet, and the center of the through-hole or the gap of the yoke. When the MRI apparatus is not provided, the beam is incident on the irradiation device perpendicularly to the rotation axis of the gantry. There is a scanning magnet on the beam axis, and the center of the irradiation field coincides with a point on the beam axis. On the other hand, since the particle beam is bent by the influence of the magnetic field of the MRI apparatus, the incident angle to the irradiation device, the position of the scanning magnet, and the center of the through-hole or the gap of the yoke are determined on the assumption that the particle beam is bent. As a result, it is possible to minimize the excitation amount required for the scanning magnet for realizing the required size of the irradiation field and minimize the size of the through-hole or the gap of the yoke. The incident angle to the irradiation device can be adjusted by the excitation amount of the bending magnet 16.

REFERENCE SIGNS LIST 1 charged particle beam generation device
2 beam transport system
3 linac
4 synchrotron
5 radio frequency application device
6 acceleration device
7 control system (control device)
11 emission deflector
12 beam path
14, 15, 16 bending magnet
17 therapy room
21 irradiation device
24 couch (bed)
25 irradiation object
26 irradiation target
30 particle beam monitor
31, 32 scanning magnet
33 dose monitor
34 position monitor
40 X-ray CT device
41 Irradiation planning system
42 database
50 magnet
51 coil
52 magnetic pole
60 yoke
150 MRI apparatus

The invention claimed is:

1. A particle beam therapy system comprising:
a bed on which an irradiation object is mounted;
an irradiation device that irradiates an irradiation target in the irradiation object with a particle beam;
a rotary gantry on which the irradiation device is mounted and which rotates around the bed; and
a magnetic resonance imaging apparatus that captures an image of the irradiation object,
wherein the magnetic resonance imaging apparatus includes a static magnetic field generation device,
wherein the static magnetic field generation device includes:
a magnet that generates a static magnetic field in an image capturing space in which the irradiation target is disposed, and
a yoke that is disposed outside the image capturing space and through which a magnetic flux of the magnetic field generated by the magnet passes,
wherein the irradiation device is disposed on a back surface side of the yoke when viewed from the image capturing space, and irradiates the irradiation target with the particle beam through a through-hole provided in the yoke or a gap provided in the yoke,
wherein a direction in which the particle beam enters the image capturing space is perpendicular with a direction of a magnetic flux of the static magnetic field applied to the image capturing space by the magnet,
wherein the magnetic resonance imaging apparatus is disposed in a space on an inner side of the rotary gantry,
wherein the irradiation device includes a particle beam monitor that is disposed on a central axis of the particle beam and detects the particle beam, and
wherein the particle beam monitor is disposed between the yoke and the rotary gantry.

2. The particle beam therapy system according to claim 1, wherein a pair of the magnets are disposed facing each other with the image capturing space interposed between the magnets, and
wherein the yoke has a columnar shape disposed between the pair of magnets.

3. The particle beam therapy system according to claim 2,
wherein the through-hole is provided at a center of the columnar yoke in a width direction, and
wherein the columnar yoke on both sides of the through-hole is provided with a protrusion having a width or a depth more than a width or a depth of a portion at which the through-hole is not disposed.

4. The particle beam therapy system according to claim 1, further comprising:
a rotary gantry on which the irradiation device is mounted and which rotates around the bed,
wherein the magnetic resonance imaging apparatus is disposed in a space on an inner side of the rotary gantry, is supported by the rotary gantry, and rotates around the bed together with the irradiation device.

5. The particle beam therapy system according to claim 3, wherein the rotary gantry includes:
a support that detachably supports the magnetic resonance imaging apparatus, and
a rail that moves the magnetic resonance imaging apparatus detached from the rotary gantry, in a direction separated from the bed.

6. The particle beam therapy system according to claim 5, wherein a direction in which a transport mechanism transports the magnetic resonance imaging apparatus is an axial direction of the rotary gantry.

7. The particle beam therapy system according to claim 1, wherein in the irradiation device, a chamber filled with a gas is further disposed on the central axis of the particle beam between the particle beam monitor and the yoke, and
wherein the chamber guides the particle beam having passed through the particle beam monitor to the through-hole and emits the particle beam from a tip of the chamber toward the irradiation target.

8. The particle beam therapy system according to claim 7, wherein the tip of the chamber is inserted into the through-hole.

9. The particle beam therapy system according to claim 7, wherein the tip of the chamber is configured to be able to have a structure of being retracted outward from the through-hole.

10. The particle beam therapy system according to claim 6,
wherein the magnet is a superconducting magnet including a superconducting coil or a normal conducting magnet including a normal conducting coil, and
wherein the magnetic resonance imaging apparatus includes a demagnetization device that demagnetizes the magnet by stopping a current flowing through the superconducting coil or the normal conduction coil when a transport mechanism transports the magnetic resonance imaging apparatus.

11. The particle beam therapy system according to claim 1, further comprising:
a controller that controls an irradiation timing of the particle beam based on an image captured by the magnetic resonance imaging apparatus.

12. The particle beam therapy system according to claim 1,
wherein a direction of the magnetic field of the magnet is reversed to change a direction of curvature of the particle beam.

13. The particle beam therapy system according to claim 1,
wherein the magnet has a cylindrical shape,
wherein the image capturing space is formed inside the cylindrical magnet,
wherein the yoke is disposed on an outer surface of the cylindrical magnet,
wherein a second through-hole is provided in the cylindrical magnet so as to overlap the through-hole of the yoke, and
wherein the particle beam passes through the first and second through-holes and is applied to an irradiation target in the image capturing space.

14. A particle beam therapy system, comprising:
a bed on which an irradiation object is mounted;
an irradiation device that irradiates an irradiation target in the irradiation object with a particle beam;
a rotary gantry on which the irradiation device is mounted and which rotates around the bed;
a magnetic resonance imaging apparatus, which includes:
a magnet that generates a static magnetic field in an image capturing space in which an irradiation target of a particle beam is disposed; and
a yoke through which a magnetic flux generated from the magnet passes,
wherein the yoke is provided with a through-hole through which the particle beam passes,
wherein a direction in which the particle beam enters and passes through the through-hole to the image capturing space is perpendicular with a direction of a magnetic flux of the static magnetic field applied to the image capturing space by the magnet,
wherein the irradiation device includes a particle beam monitor that is disposed on a central axis of the particle beam and detects the particle beam, and
wherein the particle beam monitor is disposed between the yoke and the rotary gantry.

* * * * *